United States Patent
Johnsen et al.

(10) Patent No.: US 9,629,702 B2
(45) Date of Patent: *Apr. 25, 2017

(54) POROUS MATERIAL FOR INSERTION CLEANING OF INSTRUMENTS

(71) Applicant: JORDCO, INC., Beaverton, OR (US)

(72) Inventors: James B. Johnsen, Beaverton, OR (US); Hal J. Oien, Tualatin, OR (US)

(73) Assignee: Jordco, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/752,689

(22) Filed: Jun. 26, 2015

(65) Prior Publication Data

US 2016/0081780 A1 Mar. 24, 2016

Related U.S. Application Data

(63) Continuation of application No. 14/165,536, filed on Jan. 27, 2014, now Pat. No. 9,066,776, which is a continuation of application No. 13/562,110, filed on Jul. 30, 2012, now Pat. No. 8,635,735, which is a continuation of application No. 10/350,640, filed on Jan. 23, 2003, now Pat. No. 8,231,734.

(60) Provisional application No. 60/417,802, filed on Oct. 10, 2002.

(51) Int. Cl.
*A61C 3/00* (2006.01)
*A61C 19/00* (2006.01)
*A47L 25/00* (2006.01)
*A61C 5/02* (2006.01)
*G09F 3/04* (2006.01)
*B08B 1/00* (2006.01)

(52) U.S. Cl.
CPC ............ *A61C 19/002* (2013.01); *A47L 25/00* (2013.01); *A61C 3/00* (2013.01); *A61C 5/025* (2013.01); *B08B 1/001* (2013.01); *G09F 3/04* (2013.01)

(58) Field of Classification Search
CPC A47L 25/00; A61C 3/00; A61C 5/025; A61C 19/002; B08B 1/001
See application file for complete search history.

(56) References Cited

U.S. PATENT DOCUMENTS

| 5,368,482 A * | 11/1994 | Johnsen | A61C 19/006 206/63.5 |
| 5,967,778 A * | 10/1999 | Riitano | A61C 19/002 206/366 |
| 6,036,490 A * | 3/2000 | Johnsen | A61C 5/025 433/102 |
| 6,257,888 B1 * | 7/2001 | Barham | A61C 19/006 206/63.5 |
| 6,681,925 B2 * | 1/2004 | Fischer | A61B 19/0262 206/369 |

* cited by examiner

*Primary Examiner* — Randall Chin
(74) *Attorney, Agent, or Firm* — Kolisch Hartwell, P.C.

(57) ABSTRACT

A porous material for insertion cleaning of instruments is provided, such porous material including an at least partially open-cell foam body and a surface configured to enable an instrument having contaminants to be inserted into the body. The body may be configured to substantially grip the instrument to remove a substantial portion of the contaminants from the instrument.

1 Claim, 2 Drawing Sheets

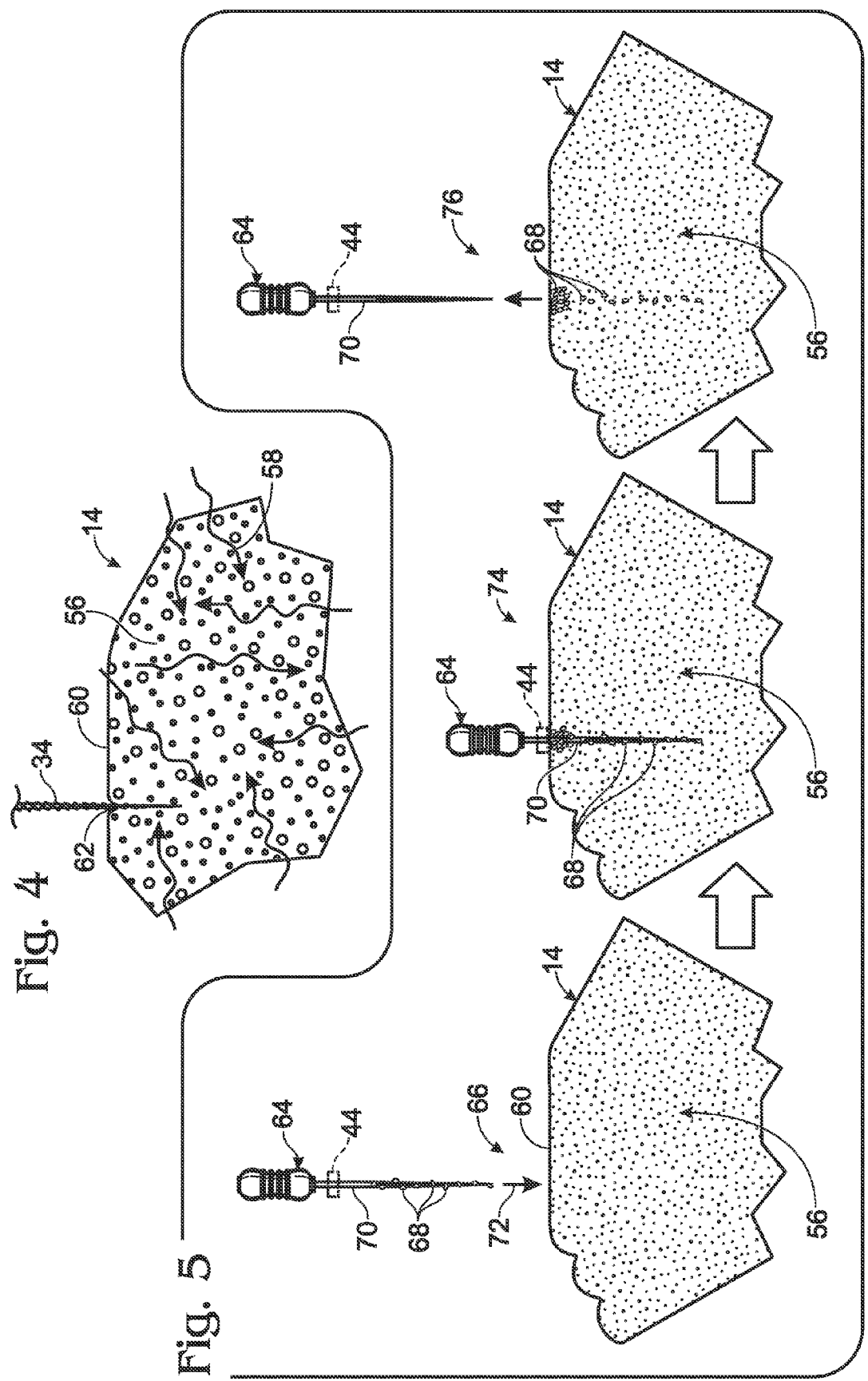

POROUS MATERIAL FOR INSERTION CLEANING OF INSTRUMENTS

CROSS-REFERENCE TO RELATED APPLICATIONS

This application is a continuation of U.S. patent application Ser. No. 14/165,536 filed Jan. 27, 2014, issued as U.S. Pat. No. 9,066,776 on Jun. 30, 2015, which is a continuation of U.S. patent application Ser. No. 13/562,110 filed Jul. 30, 2012, issued as U.S. Pat. No. 8,635,735 on Jan. 28, 2014, which is a continuation of U.S. patent application Ser. No. 10/350,640 filed Jan. 23, 2003, issued as U.S. Pat. No. 8,231,734 on Jul. 31, 2012, which claims priority to U.S. Provisional Patent Application Ser. No. 60/417,802 filed Oct. 10, 2002, the disclosures of which are hereby incorporated by reference in their entireties.

BACKGROUND AND SUMMARY

Various industries may use different types of instruments. In some industries, the instruments may need to be maintained in a substantially clean state during use. However, use of the instruments may expose the instruments to different types of contaminants, including biocontaminants, dust, dirt, grime, etc. It may be desired to quickly and effectively reduce the level of contaminants on the instruments prior to, during or after use. For example, in the medical and/or dental fields, instruments may need to be cleaned prior, during and after medical and/or dental procedures.

As an example, dental instruments may require periodic servicing during a dental maintenance and/or treatment procedure, such as an endodontic procedure. In an endodontic procedure, dentists must have ready access to instruments, such as endodontic files. The endodontic files may be used to gauge the depth of root canals prepared in a patient's teeth. Typically, a dental assistant is employed to hold a file dispenser from which the dentist can withdraw sterile endodontic files.

During the endodontic procedure, the endodontic files may collect pulpal tissue, dentin shavings and/or various medicaments. To clean such materials from the endodontic files, a dental assistant may be required to wipe the instruments with a gauze sponge. Wiping the instrument with such a sponge may be inadequate to clean the instruments and may be cumbersome for the dental assistant.

SUMMARY

A porous material for insertion cleaning of instruments is provided, such porous material including an at least partially open-cell foam body and a surface configured to enable an instrument having contaminants to be inserted into the body. The body may be configured to substantially grip the instrument to remove a substantial portion of the contaminants from the instrument.

BRIEF DESCRIPTION OF THE DRAWINGS

FIG. 4 is a schematic illustration of some of the characteristics of the porous material of FIG. 1.

FIG. 5 is a schematic illustration of the use of the porous material shown in FIG. 3 to insertion clean an instrument.

DETAILED DESCRIPTION

As disclosed herein, a porous material is provided that enables insertion cleaning of instruments. The porous material may be used to clean instruments from a variety of industries, including, but not limited to, high-technology industries, medical industries, dental industries, etc. Although the following description illustrates the use of a porous material in a dental instrument servicing system, it should be appreciated that a similar porous material may be used in other types of medical, dental and high-technology instrument cleaning systems.

For illustration purposes, the porous material may be mounted in such dental instrument servicing systems described and disclosed in the following patents: U.S. Pat. No. 4,280,808 to Johnsen and Oien entitled "Endodontic File Holder" issued Jul. 28, 1981; U.S. Pat. No. 5,368,482 to Johnsen and Oien entitled "Dental Instrument Servicing System" issued Nov. 29, 1994; and U.S. Pat. No. 6,036,490 to Johnsen and Oien entitled "Dental Instrument Servicing System" issued Mar. 14, 2000, the disclosures of which are hereby incorporated by reference. Although described in the context of a dental instrument servicing system, it should be appreciated that the porous material described below may be used alone or in other types of servicing systems.

Figure 1:
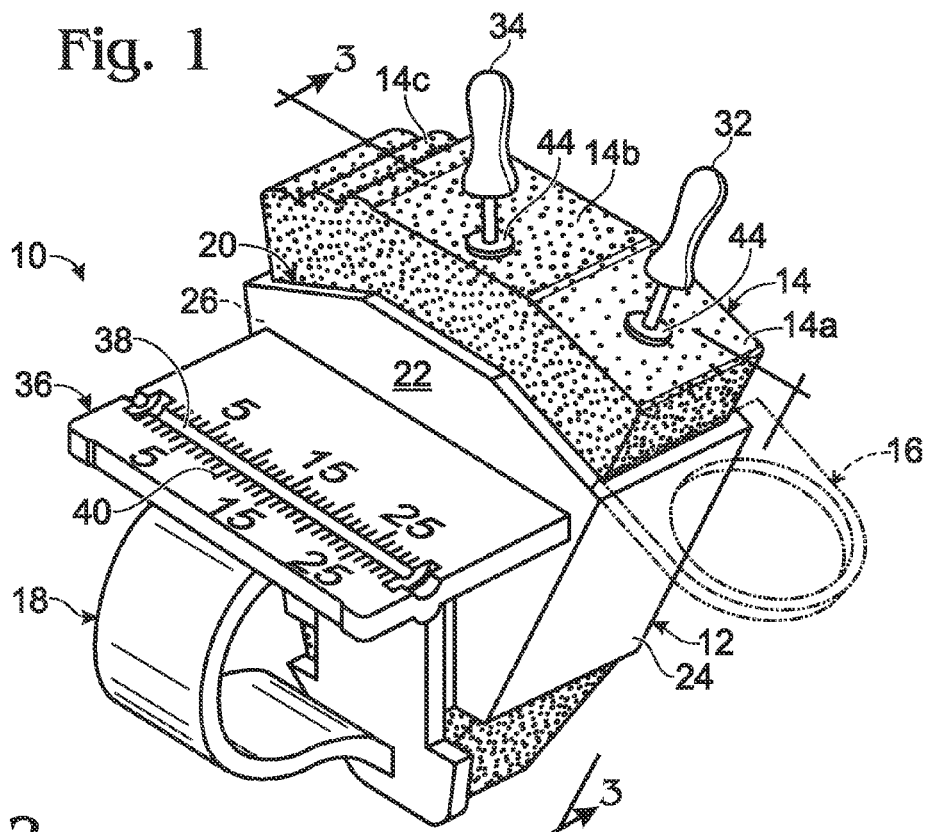
FIG. 1 is an isometric view of a dental instrument servicing system including a cushion constructed of a porous material according to an embodiment of the present invention.

An exemplary dental instrument servicing system 10 is shown generally in FIG. 1. As shown, system 10 may include a socket-forming member 12, which in turn may carry an insert or cushion 14. The system may further optionally include a medicament holder 16 and a finger mount 18. The cushion, medicament holder and finger mount may be selectively removable from the socket-forming member.

Socket-forming member 12 may define a double-open-ended socket 20, which provides a seat for cushion 14. Although not required, the socket-defining member may be of unitary construction, being formed of a lightweight material such as plastic or aluminum. These materials, it will be appreciated, typically are inexpensive, may be formed by molding processes, and may be suitable for hand-worn use.

Socket-forming member 12 may include plural walls that define socket 20. For example, socket 20 may be defined by front wall 22, side walls 24, 26 and back wall 28 (shown in FIG. 2). Typically, the cushions are somewhat abrasive such that the abrasiveness of the cushion provides frictional adherence of the cushion to the walls of the socket-forming member. In some embodiments, cushion 14 may be removably inserted into socket 20 and retained by one or more of the walls of socket forming member 12. Additionally, in some embodiments, projections (shown in FIG. 3 at 30) may extend outward from side walls 24, 26 and may provide frictional anchors, which may help to maintain cushion 14 within socket 20.

As illustrated, cushion 14 may be generally pie-shaped such that it conforms closely to the shape of the socket. However, it should be appreciated that cushion 14 may be any suitable shape depending on the system.

The upper end of socket-forming member 12 may be of a predetermined contour. For example, the socket-forming member may define a plurality of distinct regions, each of which may accommodate different servicing operations. The distinct regions may face in different angular directions.

Cushion 14 may include a plurality of distinct cushion surface regions 14a, 14b and 14c. These cushion surface regions may substantially mimic the contour of the upper end of the socket-forming member 12. Each cushion surface region may be adapted to receive files of a predetermined size and/or style. Therefore, the system may be used to organize endodontic files, or other instruments, by placement of selected files into predetermined cushion surface regions.

In FIG. 1, for example, file 32 is placed in right-most region 14a, whereas file 34 is in central region 14b. It should be noted that the cushion surface regions may include a substantially planar surface (as shown in reference to 14a and 14b) or may be contoured. Contoured surfaces may provide additional surface area for organizing and placing instruments. For example, cushion surface region 14c undulates providing additional distinct regions for placing instruments.

Finger mount 18 also may be attached to socket-forming member 12. Finger mount 18 may allow the system to be positioned on an individual's forefinger for use during a dental procedure. The finger mount may be removably attached to socket-forming member 12 via a cooperative slide arrangement, as described in previously issued U.S. Pat. No. 4,280,808, which has been incorporated by reference above. Typically, such a system is relatively lightweight and is not appreciably more burdensome than a large ring. Thus, such a system typically will not significantly interfere with use of the wearer's hand.

Socket-forming member 12 also may include an outwardly projecting shelf 36. The shelf may extend outward covering finger mount 18 and may protect a user's finger from injury by sharp instruments, such as endodontic files, which may be inserted into the cushion. The shelf may further serve as a measuring device for use in connection with endodontic files. Thus, shelf 36 may include a trough 38 for receipt of endodontic files. A scale 40 may be etched into shelf 36, accommodating accurate positioning of depth markers on the file. The use of such a measuring device is more fully described in the aforementioned U.S. Pat. No. 4,280,808, which has been incorporated herein by reference above.

As briefly described above, medicament holder 16 may be removably applied to socket-forming member 12. Medicament holder 16 may include a cup section configured to hold a medicament in a dosage container and a clip section (not shown) configured to selectively attach the medicament holder to the socket-forming member.

Figure 2:
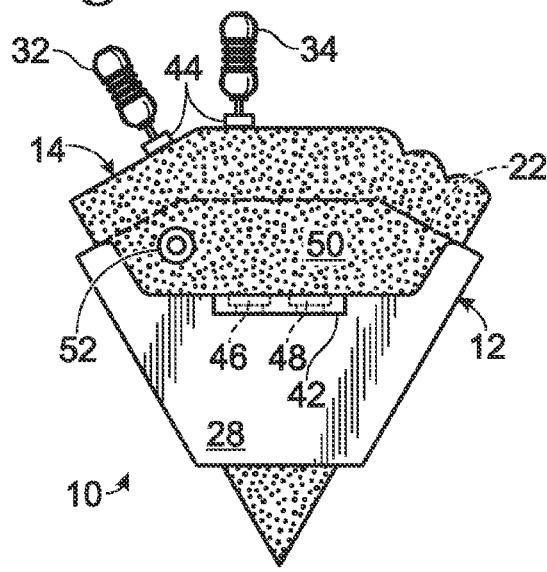
FIG. 2 is a rear view of the dental instrument servicing system shown in FIG. 1 including a lowered back wall forming an enlarged instrument docking area.

Referring to FIG. 2, socket-forming member 12 further may include a service platform 42. Service platform 42 may project from back wall 28. The service platform may be adapted for receipt of depth markers 44. Depth markers 44 may be used in connection with endodontic files 32, 34. As indicated, service platform 42 may include one or more recessed openings 46, 48, each of which may be configured to hold one or more depth markers 44 for application to endodontic files. A depth marker may be applied to an endodontic file by insertion of the endodontic file through an aperture formed in recessed openings 46, 48.

FIG. 2 also illustrates that back wall 28 may be lowered relative to front wall 22 to provide for an enlarged docking area 50 for endodontic files. The docking area provides for an increased area to place files and other instruments. Thus, an instrument, such as endodontic file 52, may be inserted substantially perpendicular to the direction that files 32 and 34 are shown positioned in cushion 14. Such a docking area may enable, a dental assistant to perform a safe pick up without causing the doctor to break his/her visual field while operating under a surgical microscope. Moreover, the presence of the taller front wall 22 may operate as a safety shield. Thus, front wall 22 may shield the dental instrument servicing system wearer, such as the dental assistant, from endodontic files that are inserted into docking area 50 of cushion 14.

Figure 3:
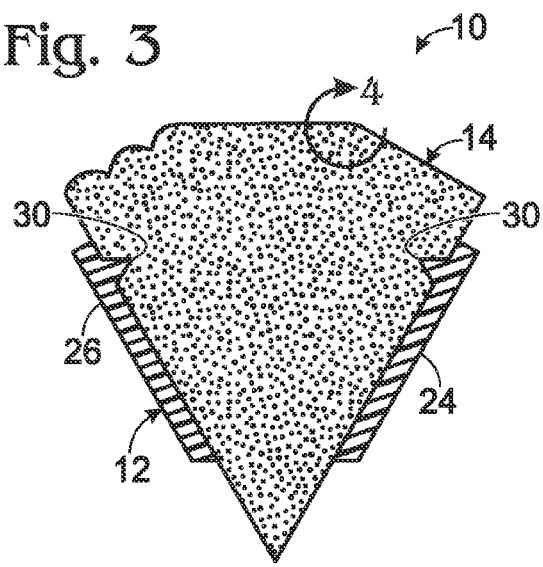
FIG. 3 is a cross-sectional side view of the dental instrument servicing system of FIG. 1 taken generally along line 3-3 of FIG. 1.

FIG. 3 further illustrates cushion 14. As described in more detail below, cushion 14 is formed of a porous material, such as foam, suitable for use in holding and cleaning instruments, such as endodontic files. Tests have been conducted to determine the suitable composition for cushion 14. Exemplary foams are described in TABLE 1 below:

TABLE 1

| Foam | Foam A | Foam B |
| --- | --- | --- |
| Density (kg/m$^3$) (kilograms per cubic meter) | 25.6 ± 2 kg/m$^3$ | 22.4 ± 2 kg/m$^3$ |
| Material | Urethane | Urethane |
| Cell Count (cells/cm) (cells per centimeter) | 15-16 cells/cm | 15-16 cells/cm |
| Air Flow (dm$^3$/sec) (cubic decimeters per second) | 4.1 dm$^3$/sec | 3.8 dm$^3$/sec |
| 25% IFD (N) (Newtons) | 94.7 N | 99.08 N |
| 50% CFD (N) (Newtons) | 2.8 ± 0.2 N (0.62 ± 0.05 psi) | 2.7 ± 0.2 N (0.60 ± 0.05 psi) |

It should be appreciated that although two exemplary foams are described in detail, the composition of suitable cushions may vary. For example, suitable foams for use in the present system may have a different density, air flow, indentation force deflection (IFD), compression force deflection (CFD), cell count, etc. Foam A and Foam B, as described above, are included only for illustrative purposes and are not intended to include all suitable compositions for cushion 14.

Generally, the foam characteristics may be balanced to achieve a suitable material for use in insertion cleaning of instruments. Selection of one or more of the density, material, and cell count of the foam may effect a change in the air flow, the indentation force deflection, the compression force deflection, or other characteristic of the cushion. For example, selection of the appropriate material may include balancing the density and cell count of the foam, such that the foam functions as desired.

However, it is noted that suitable foams for cushion 14 typically have a density in the range of 20 kg/m$^3$ to 30 kg/m$^3$. For example, and as shown above, Foam A has a density of 25.6±2 kg/m$^3$ and Foam B has a density of 22.4±2 kg/m$^3$. Foams that are too dense may inhibit easy insertion and removal of instruments into the cushion. Likewise, and as described in more detail below, foams that are not dense enough, may not properly clean instruments when they are inserted into and removed from the cushion.

In some embodiments, the cushion may be composed of polyurethane. Polyurethane cushions may be able to withstand steam autoclaving without substantially deforming, melting, or producing any noxious out-gassing of toxic substances during the steam autoclaving process. Moreover, polyurethane is widely and safely used in many medical and dental applications.

As briefly noted above, in some embodiments, it may be desirable to sterilize the cushions (and the instruments) prior to use. For example, in many environments, steam autoclaving may be used to sterilize the cushions. Thus, the cushions may be configured to withstand sterilization via steam autoclaving prior to use. Due to the use of the cushions in medical and dental applications, the cushions typically may be configured to withstand steam autoclaving as performed in clinical environments, where the steam autoclaves typically operate within a range of between 275 degrees and 300 degrees Fahrenheit and a range of between 20 psi and 30 psi.

As shown in FIG. 4, the cushions may include an at least partially open-cell foam body. The at least partially open-cell body may allow steam from an autoclave to penetrate an interior region 56 of the cushion. Penetration of the interior region enables steam to surround and effectively sterilize endodontic files or other instruments at least partially disposed within the cushion. Arrows 58, shown in FIG. 4, illustrate passageways through which steam may pass through the open-cell structure of the cushion to the interior region of the cushion, thereby fully penetrating the cushion with steam from the autoclave. It should be noted that the arrows are intended only for illustrative purposes.

Typically, substantially closed cell structures prevent steam from passing into the interior region of the cushion. Such closed cell cushions may not provide the necessary sterilization of the instruments positioned within the cushion. In contrast, cushions that have an air flow of more than approximately 1.0 dm$^3$/second (as measured according to standard ASTM D 3574 Air Flow Test G) may be adequate to enable sterilization of endodontic files positioned in the interior region of the cushion. Typically, suitable cushions will have an air flow range of approximately 1.0 dm$^3$/second to 4.5 dm$^3$/second according to ASTM D 3574 Air Flow Test G. Two exemplary cushions are described in TABLE 1 (shown above), specifically, Foam A has an air flow of 4.1 dm$^3$/second and Foam B has an air flow of 3.8 dm$^3$/second.

As illustrated, cushion 14 typically includes a surface 60 configured to enable an instrument to be inserted into the body of the cushion. Instruments, such as file 34, may puncture surface 60 and be pushed into interior region 56 of the cushion. Typically, surface 60 is resilient, such that surface 60 is able to recover from the puncture and return to its prior state.

In FIG. 4, an endodontic file 34 is shown being inserted into cushion 14. The tip of file 34 thus may be seen to penetrate surface 60 and slide through the body into the interior region. The foam may be configured to enable such files, or other instruments, of varying shaft diameters and lengths, to easily penetrate the cushion. Typically, the cushions are "crisp" or "firm" such that the tip of the instrument easily pierces the surface (indicated at 62). Such cushions adequately resist collapsing when penetrated by an instrument. Materials that collapse, or that resist the penetration of files or other instruments, may frustrate the user and may require additional user attention during use.

The "firmness" of the cushions may be measured using the 25% indentation force deflection (IFD) test according to standard ASTM D 3574 Test B. An IFD number represents the force required to indent a foam sample by a specified percentage (e.g. 25%) of its original thickness. Cushions for receipt of endodontic files typically have a 25% indentation force deflection of approximately at least 80.00 N. Generally, the cushions will have an indentation force deflection range of approximately 80.00 N to 120.00 N, and typically between 92.00 N to 100.00 N. As shown in TABLE 1 above, suitable foams have a 25% indentation force deflection of approximately 94.7 N and 99.08 N.

It further should be noted that the foam within the cushions may be described in relation to their compression force deflection (CFD) values. CFD values may be obtained by determining the force required to compress an entire sample surface area to 50% of its sample height. As shown in TABLE 1 above, exemplary Foam A has a CFD value of 2.8±0.2 N and exemplary Foam B has a CFD value of 2.7±0.2 N. Foams with other CFD values may be suitable, providing that the material enables smooth insertion of instruments into the cushion.

FIG. 5 schematically illustrates the instrument cleaning properties of the cushions. Generally, the abrasive action of the foam in a cushion functions to substantially clean instruments inserted therein. More specifically, the porous material in the cushion is configured to grip an instrument, such as a dental file (indicated generally at 64 in FIG. 5), and clean its flutes and ridges, as the instrument is inserted into, and pulled out of, the porous material. The gripping characteristics of the porous material substantially decrease contaminants and other residuals on the instrument.

For example, as shown in FIG. 5 at 66, during a medical or dental procedure, an instrument, such as file 64, may accumulate contaminants, such as bioburdens 68. Bioburdens, such as pulpal tissue, dentin shavings and various medicaments may cling to the file. For example, bioburdens 68 may extend along shaft 70 of file 64. Insertion of file 64 into cushion 14 may occur by penetrating surface 60, as indicated by arrow 72.

Insertion of file 64 into cushion 14 results in shaft 70 extending at least partially into the interior region 56 of cushion 14. Bioburdens 68, or other contaminants, may be sloughed off of shaft 70 as it is inserted into the cushion. Specifically, the cells within the cushion are configured to substantially grip the instrument as it is inserted into and pulled out of the cushion. By gripping the instrument as it is moved into and out of the cushion, bioburdens 68 may be displaced from the instrument to the cushion.

The composition of the cushion will affect the removal of bioburdens and other contaminants from the instrument. Cushions that are more open-celled in architecture may be less effective in removing contaminants from instruments. Typically, cushions composed of foam having a cell count in the range of 12 cells/cm to 20 cells/cm have been found to be adequate in removing a substantial portion (e.g. over 90%) of contaminants from a contaminated instrument. Specifically, as shown in TABLE 1 above, foams, such as Foam A and B, which have cell counts of 15 cells/cm to 16 cells/cm, function to significantly reduce contaminants on an instrument.

Removal of the dental instrument from cushion 14 results in bioburdens 68 being left in cushion 14, as shown generally at 76. Specifically, shaft 70 of file 64 is substantially free of bioburdens 68. Further cleaning of file 64 may include reinsertion of shaft 70 into cushion 14, thereby repeating the steps illustrated generally at 66, 74 and 76 in FIG. 5. Multiple insertions of the dental instrument into the cushion may function to substantially decrease the level of bioburdens or other contaminants on file 64.

The cleaning effectiveness of the exemplary cushions is illustrated in TABLE 2 below. Specifically, the cleaning effectiveness was measured using biological serial dilution techniques. Accordingly, the level of bioburdens on the instrument was measured prior to, and after, insertion and removal (also referred to herein as a stab) of the instrument into and out of the cushion. As shown in TABLE 2 below, an 82.6% spore reduction level (level of bioburdens on the instrument) was achieved after a first stab of the instrument into Foam A and B. A second stab increased the spore reduction level to 86.3%. A 96% spore reduction level was achieved after three insertions (or stabs) of the instrument into Foam A and B.

TABLE 2

| Foam | Foam A | Foam B |
|---|---|---|
| Spore Reduction: 1 Stab | 82.6% | 82.6% |
| Spore Reduction: 2 Stabs | 86.3% | 86.3% |
| Spore Reduction: 3 Stabs | 96.3% | 96.3% |

While the present description has been provided with reference to the foregoing embodiments, those skilled in the art will understand that many variations may be made therein without departing from the spirit and scope defined in the following claims. The description should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element or the equivalent thereof, such claims should be understood to include incorporation of one or more such elements, neither requiring, nor excluding, two or more such elements.

What is claimed is:

1. A method of cleaning a dental instrument, comprising:
providing a foam having an interior region, a surface, and an ASTM air flow specification of at least 1.0 cubic decimeter per second ($dm^3$/sec);
inserting a dental instrument through the surface and into the interior region, whereby the foam substantially grips the dental instrument; and
removing the dental instrument from the foam, whereby bioburdens are removed from the dental instrument after an insertion of the dental instrument into the foam.

* * * * *